(12) United States Patent
Leason et al.

(10) Patent No.: US 7,914,565 B2
(45) Date of Patent: Mar. 29, 2011

(54) DEVICE FOR DRAWING HEAT FROM THE SURFACE OF SKIN

(76) Inventors: David Leason, Chappaqua, NY (US);
Scott Sullivan, Palo Alto, CA (US)

( * ) Notice: Subject to any disclaimer, the term of this patent is extended or adjusted under 35 U.S.C. 154(b) by 1391 days.

(21) Appl. No.: 11/279,059

(22) Filed: Apr. 7, 2006

(65) Prior Publication Data

US 2006/0178716 A1    Aug. 10, 2006

(51) Int. Cl.
*A61F 7/00* (2006.01)
(52) U.S. Cl. ........... 607/107; 607/96; 607/108; 607/109
(58) Field of Classification Search .................... 607/96, 607/107

See application file for complete search history.

(56) References Cited

U.S. PATENT DOCUMENTS 5,634,472 A * 6/1997 Raghuprasad ................ 600/555

* cited by examiner

*Primary Examiner* — Roy D Gibson
*Assistant Examiner* — Kaitlyn E Helling
(74) *Attorney, Agent, or Firm* — Leason Ellis LLP

(57) ABSTRACT

A handheld appliance suitable for skin treatment and/or personal care operations comprises an applicator structure having a thermally conductive element supported so as to be exposable to controlled release of pressurized fluid within a gas-expansion chamber. The just-expanded gas causes an endothermic reaction in which heat is removed from the applicator. The applicator is usable to then draw heat energy from skin, etc. When applied to skin, a numbing effect is experienced which can ease pain associated with depilation, discomfort associated with exfoliation, be useful in treating wounds, etc.

16 Claims, 7 Drawing Sheets

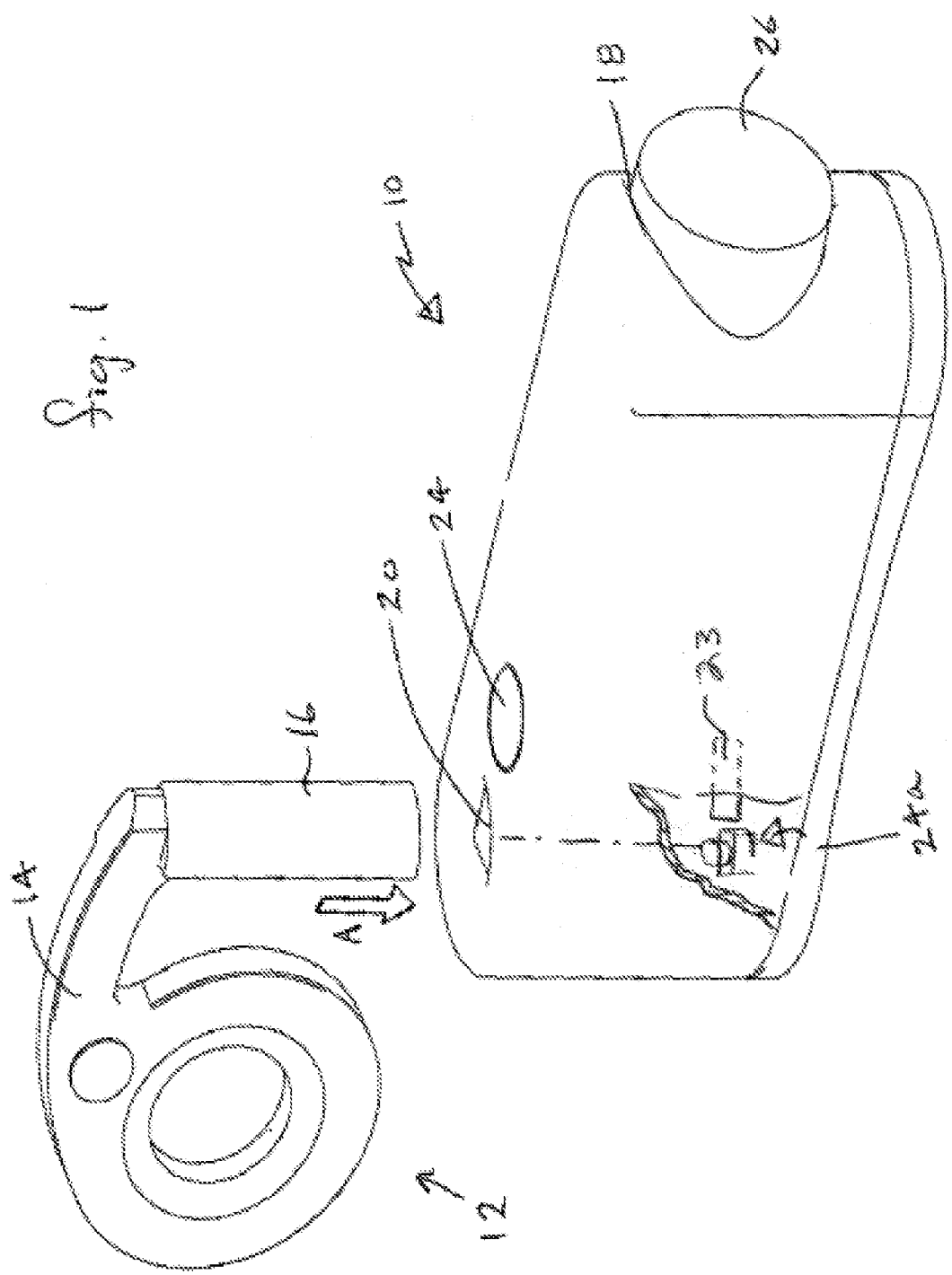

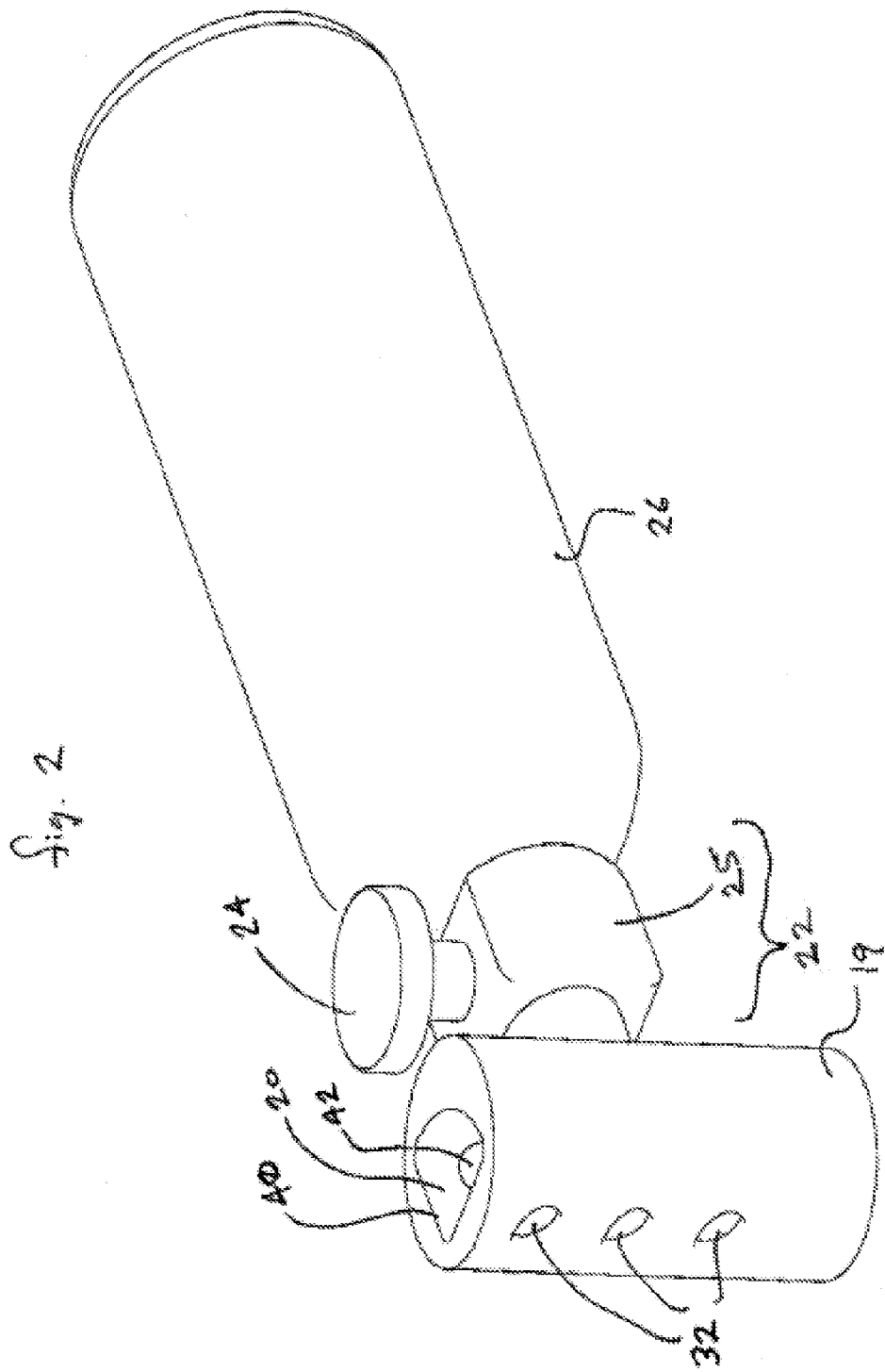

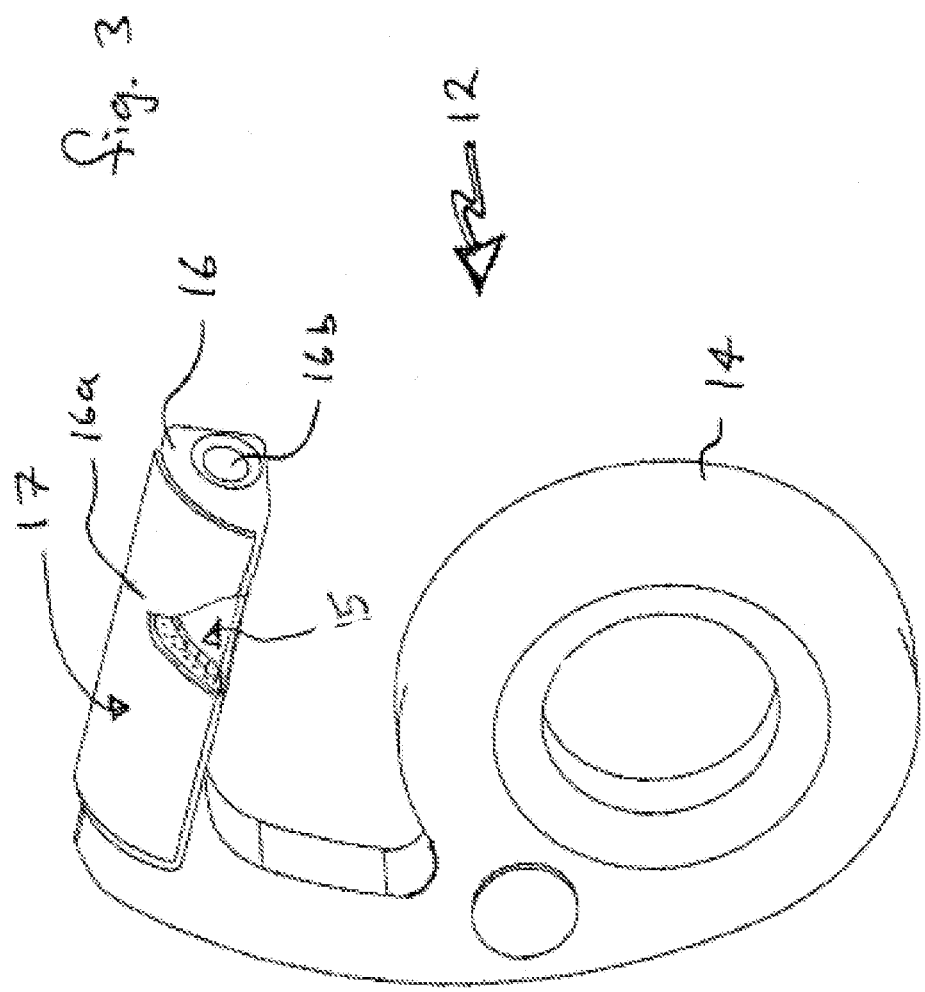

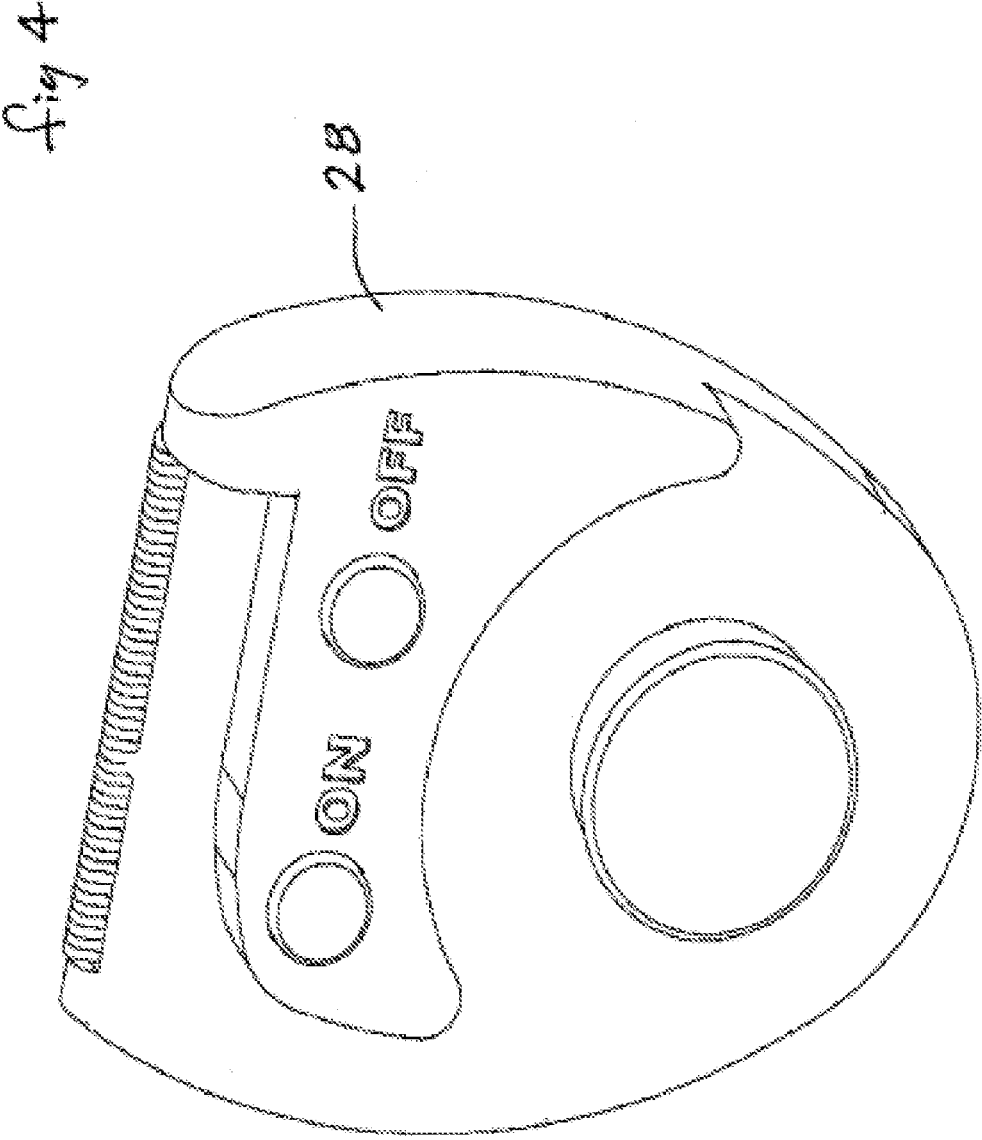

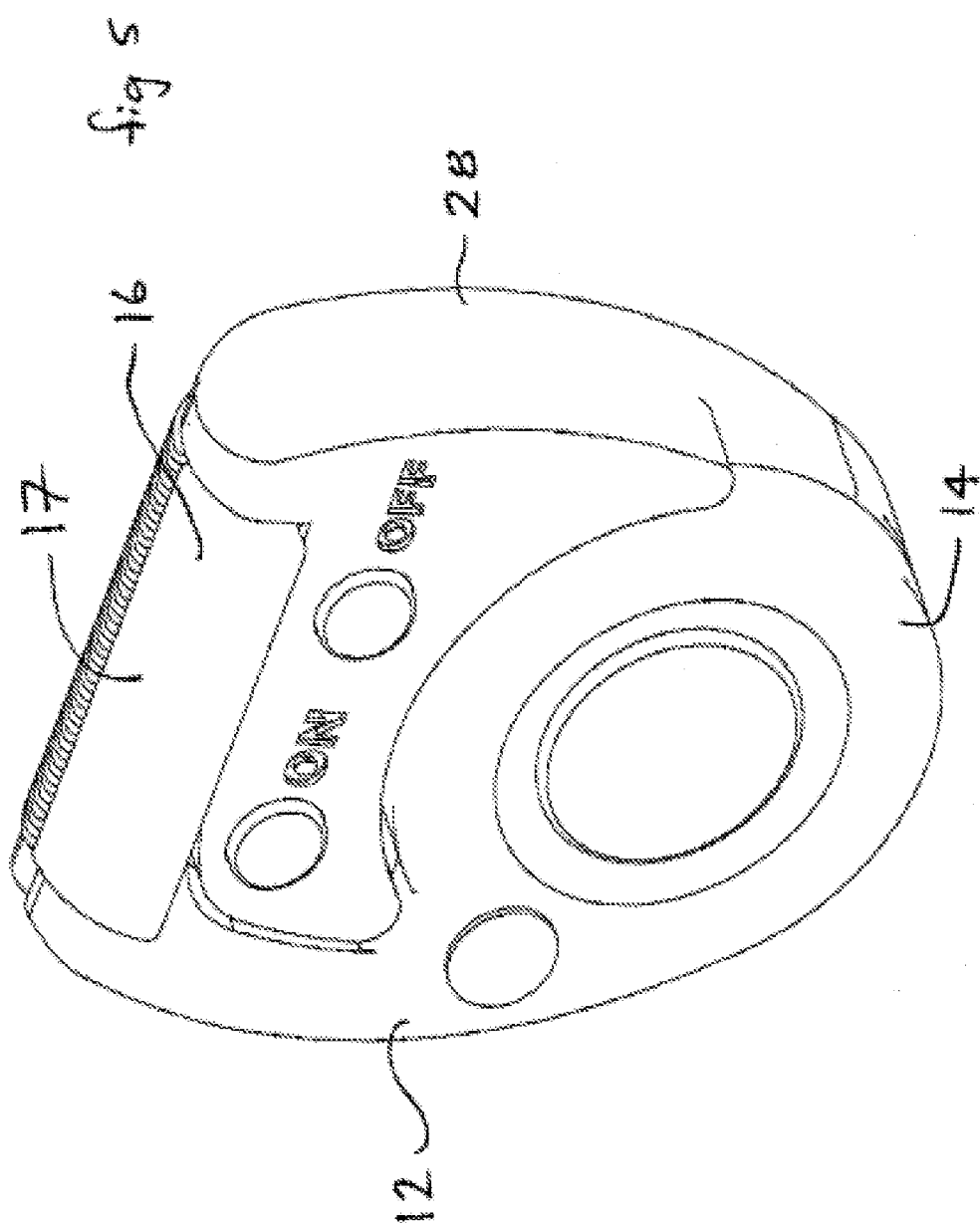

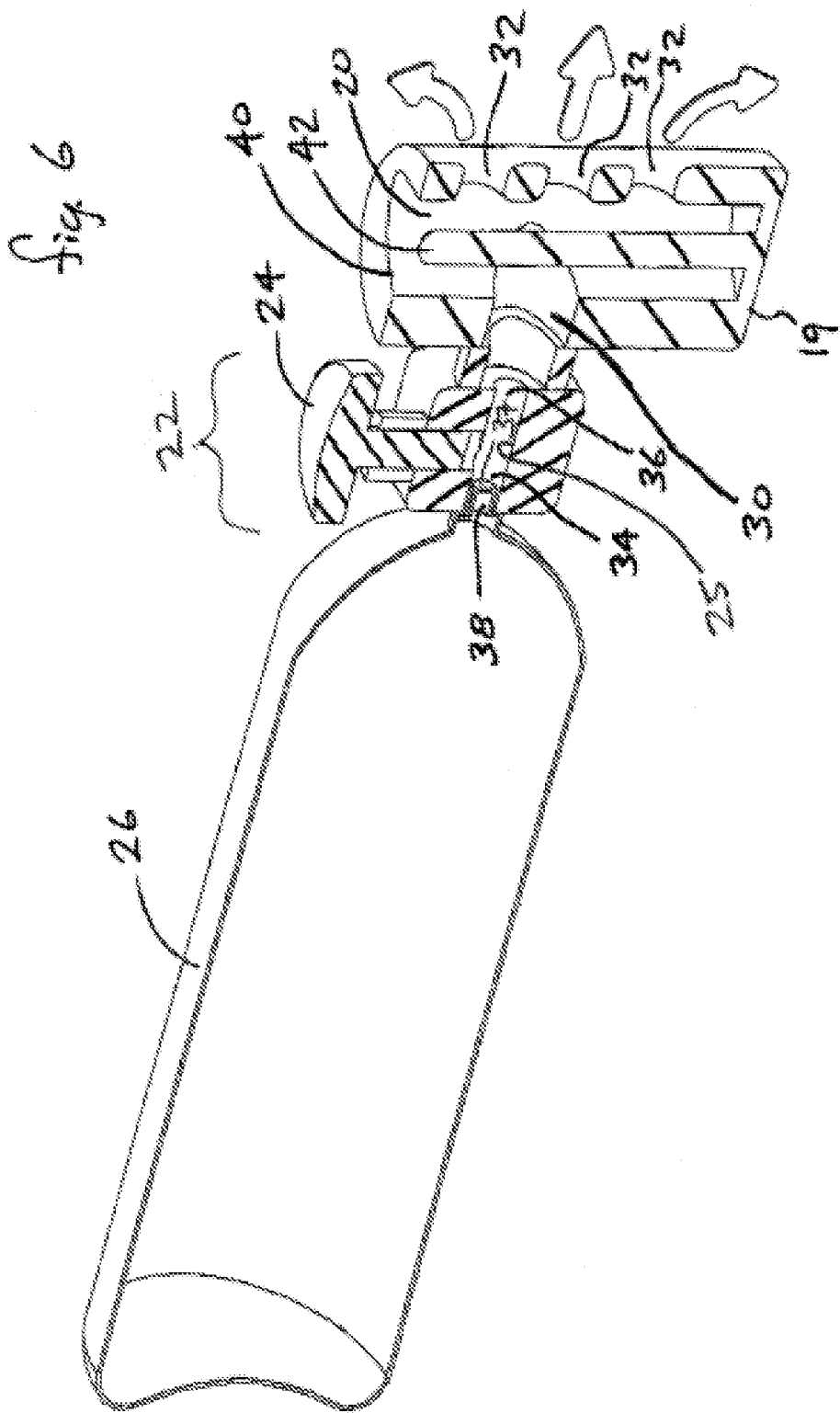

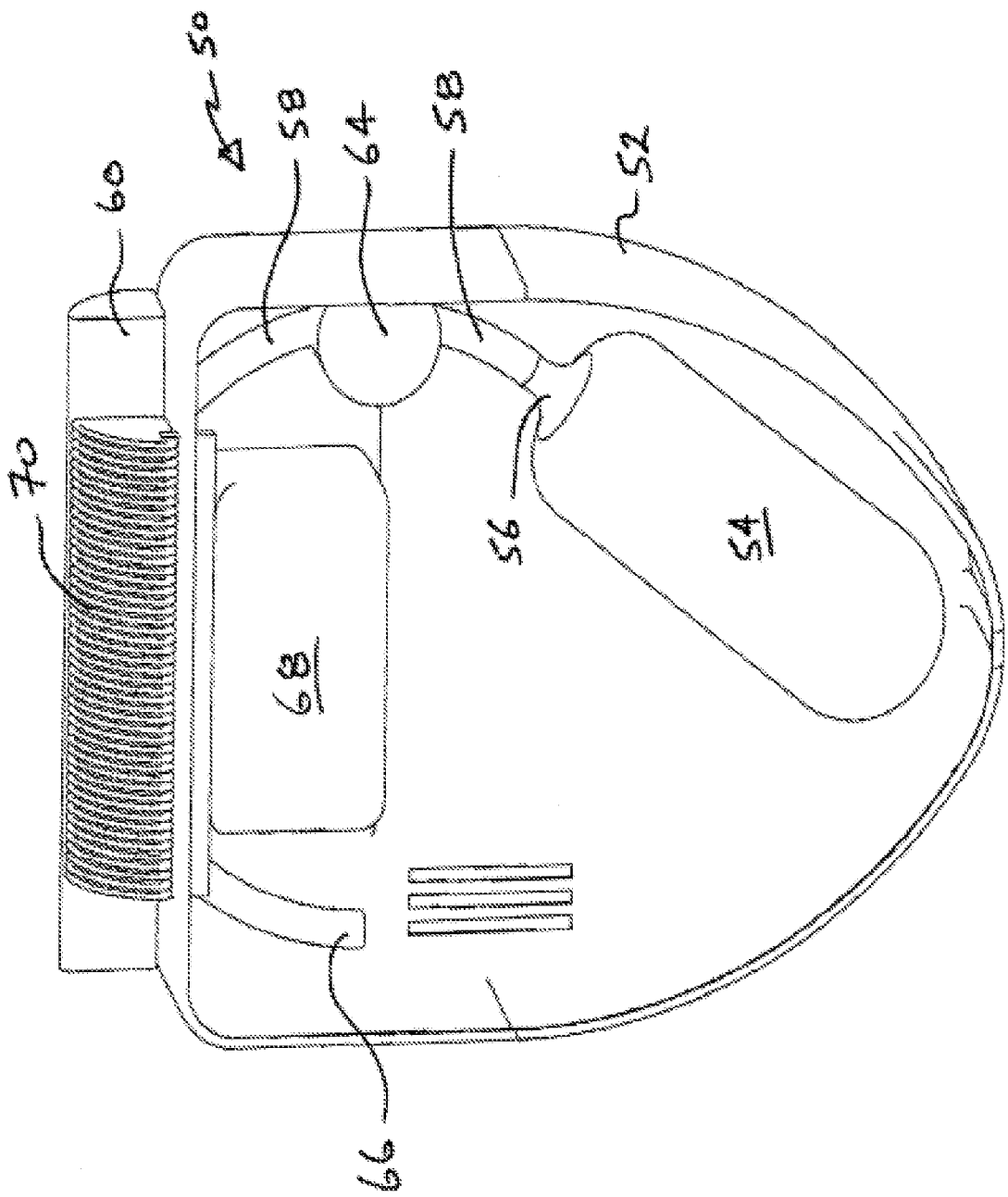

DEVICE FOR DRAWING HEAT FROM THE SURFACE OF SKIN

BACKGROUND STATEMENT

It is quite common to apply a variety of devices to the surface of skin in an effort to beautify and/or improve its health and feel. Among the many devices used are those that are designed to remove hair from the skin—so called "depilators". The mechanical versions of these devices operate to forcefully remove each hair follicle it reaches from the skin. After several treatments, such devices can be effective in reducing and eliminating hair from unwanted areas, most commonly a woman's leg. However, the use of such devices is attendant with considerable pain and discomfort due to the forceful action of the depilation mechanism.

In an effort to reduce discomfort, one recent device disposes ice in contact with the skin to be depilated, in the path of the movement of the depilation device. The ice has a light numbing effect, which reduces the user's sensitivity at the point of depilation. A problem with this approach is that depilation typically is performed in a private place such as a bathroom, yet ice is not generally available at that location. Instead, and as proposed by Philips Corporation in connection with its HP6453 Satin Ice Optima Epilator, a liquid cartridge is stored in a freezer (e.g., in the family kitchen) until such time that depilation is desired. The cartridge is then retrieved, mounted to the depilator, and then used wherever desired by the user. In order to gain any benefit from this ice treatment, therefore, the user must have planned in advance to have a liquid cartridge in the frozen state, and must be able to comfortably retrieve the cartridge without embarrassment.

There remains a need in the field of depilation to reduce discomfort in a more convenient manner, which does not require storage of grooming devices in a freezer, and which does not require such presence aforethought. The present invention satisfies these and other needs.

SUMMARY OF THE INVENTION

In accordance with a first aspect of the invention, a personal care appliance comprises a handheld device and a base unit. The handheld device includes a mechanism suitable for performing a personal care operation, which is supported by a housing in proximity to an applicator. The applicator includes a thermally conductive element. On the other hand, the base unit has a gas expansion chamber and an insertion opening sized to receive the applicator. A coupling associated with the base unit is connectable to a supply of pressurized fluid so as to selectively release the pressurized fluid into the expansion chamber. A valve disposed in the fluid path between the supply and the expansion chamber is operable to control release of any pressurized fluid into the expansion chamber.

In accordance with a second aspect of the invention, a skin treatment system is provided, substantially as described above except that the skin treatment system is free of any mechanism for performing a personal care operation. Thus, the skin treatment system comprises a handle, an applicator supported by the handle and having a thermally conductive element, a base unit, a gas expansion chamber associated with the base unit and having an insertion opening sized to receive at least the applicator, a coupling associated with the base unit which is connectable to a supply of pressurized fluid so as to selectively release the pressurized fluid into the expansion chamber, and a valve disposed in the fluid path between the supply and the expansion chamber so as to control release of any pressurized fluid into the expansion chamber.

More particular features in accordance with these first two aspects of the invention include a keyed aperture to the insertion opening such that access to the expansion chamber requires an applicator having a generally complementary shape. Among other benefits, this can prevent probing fingers from entering the gas expansion chamber.

Also, in accordance with these first two aspects of the invention, the personal care appliance and the skin treatment system have a handle that is freely movable relative to the base unit.

In accordance with a third aspect of the invention, a skin treatment device can operate to remove heat from skin (chill the skin) free of any base unit by providing a supply of pressurized fluid in the handheld device. In accordance with this aspect of the invention, a skin treatment device comprises a handle and an applicator supported by the handle. The applicator includes a thermally conductive element. A first surface of the applicator is oriented to contact the skin. A second surface of the applicator is disposed proximate to a gas expansion chamber. The handle supports a coupling which is connectable to a supply of pressurized fluid which selectively releases pressurized fluid onto the second surface of the applicator. A valve, disposed in the fluid path between the supply and the expansion chamber, operates to control release of any pressurized fluid into the expansion chamber.

More particular features in accordance with this third aspect of the invention can include a conduit connected so as to communicate fluid from the supply to the expansion chamber, a mechanism for performing a personal care operation, or a combination of these features.

A personal care appliance or skin treatment system in accordance with the invention as set forth above can be provided with an applicator having an outer layer made of a material that is different than the thermally conductive element. The applicator can be further arranged so as to be movably supported on the housing, so as to have at least a portion that comprises a flexible skin-contacting surface, so as to include a sealed chamber containing a fluid in conductive communication with the expansion chamber so as to store a heat-absorbing potential, or a combination of these features.

These and other features, aspects and advantages can be appreciated from the following written description and the accompanying drawing figures.

BRIEF DESCRIPTION OF THE DRAWINGS

FIG. 1 is a perspective view of a base unit and an applicator, partially broken away, the base unit including a housing, a trigger button, a tank, a tank cavity, and an expansion chamber, the applicator including a handle and a thermal conductive element, the applicator being shown inserted into an expansion chamber of the base unit, according to a first embodiment of the invention;

FIG. 2 is perspective view of the base unit shown without the housing to reveal details of the tank of compressed gas, a valve assembly, the trigger button, and an expansion assembly, which includes the expansion chamber, according to the first embodiment of the invention;

FIG. 3 is a perspective view of the applicator, partially broken away, showing details of the thermal conductive element including a safety bore located at one end, according to the first embodiment of the invention;

FIG. 4 is a perspective view of a representative skin-treatment device having a skin contacting element and a body that is configured with a recess that is sized and shaped to receive the applicator of FIGS. 1-3, so that the thermal conductive element can contact the user's skin immediately adjacent to the skin contacting element;

FIG. 5 is a perspective view of the skin-treatment device of FIG. 4 showing the applicator received and held within the recess;

FIG. 6 is a perspective sectional view of the base unit shown without the housing with arrows to depict the flow of compressed gas from the tank, through the valve and through the expansion chamber; and FIG. 7 is a perspective view of a handheld personal care device, according to another embodiment of the invention, having a housing that is shown open to expose components located within the housing.

DETAILED DESCRIPTION OF CERTAIN EMBODIMENTS

The present invention has utility with a variety of depilation devices, and is described in conjunction with an exemplary depilation unit in order to completely describe one application of the invention, and should not be understood as restricting the use of the inventive mechanism in conjunction with other personal care appliances that perform personal care operations such as hair removal, wound treatment, exfoliation, needle and needleless injections, and other skin treatments for the grooming, well-being, health and maintenance of a person through contact with the skin. The invention can also be used independent of any other personal care appliance to chill skin, such as to close skin pores after a facial cleanse.

Common depilation devices either apply an electric charge to hair follicles (to kill them) or mechanically engage each hair stem and yank them out of the skin. An example of the later mechanical depilator device is disclosed in U.S. Pat. No. 4,524,772 of Daar et al. In this prior art patent, a tightly coiled spring is attached to the output shaft of a motor and restrained to a curved orientation. As the motor operates, the spring rotates and, owing to its curved condition, creates many openings between individual coils of wire into which hair may become positioned. As the spring further rotates, the hair is drawn to a pinch point between the individual coils. During this operation, the pinched hair is yanked from the skin with rotation of the coil. The contents of U.S. Pat. No. 4,524,772 are hereby incorporated by reference as if its entire specification and figure were reprinted in this patent application.

Referring now to FIGS. 1 and 2, an embodiment of the invention comprises a base unit 10 and an applicator 12. Applicator 12 includes a handle 14 and a thermally conductive element 16, which defines a contact surface 17. Contact surface 17 is the portion of conductive element 16 which contacts the user's skin when in use. In use, once chilled, contact surface 17 is pressed against the user's skin and thereby reduces the skin temperature by drawing heat energy therefrom—effectively applying "cold" to the skin. The cold sensation reduces pain by numbing the skin's pain receptors.

Base unit 10 includes a tank-cavity 18, an expansion assembly 19 having an expansion chamber 20, a valve assembly 22 and a trigger 24. Expansion chamber 20 is sized and shaped to selectively receive thermally conductive element 16 of applicator 12, when it is desired to remove heat from the element 16 (i.e., chill it), as described in greater detail below. Tank-cavity 18 is sized and shaped to receive a tank or vessel 26 of compressed gas (preferably $CO_2$, but perhaps nitrogen or even compressed air). The expansion assembly 19 and the tank 26 are connectable (shown coupled in FIG. 2) by a coupling 25 which is part of the valve assembly 22 for fluid flow into the expansion assembly from the tank from an inlet 34 to an outlet 36 (see FIG. 6).

Handle 14 of applicator 12 is preferably made from a thermally insulative material, such as a suitable plastic, wood, rubber, or a combination thereof. Thermally conductive element 16, in contrast, is preferably made from a high-density and thermally conductive material (e.g., steel, copper, bronze or brass), but may also be made from other metals such as aluminum or a plastic manufactured to have thermally conductive properties. As shown in FIG. 3, thermally conductive element 16 preferably includes a longitudinal bore 16b, its function described in greater detail below.

As shown in FIG. 3, thermally conductive element 16 optionally includes an outer layer 16a of a suitable material. The purpose of this outer layer (which, for example, may be made from nylon, polyvinyl, Teflon, or other plastic) can be to provide a smooth frictionless and therefore comfortable surface to contact the user's skin. The plastic layer can be provided to help prevent the chilled element 16 from sticking to or otherwise harming the skin by controlling the gradient of thermal transfer from the user's skin to the element 16. In this way, the plastic layer can function as a controlled thermal insulator; a kind of heat-flow limiter.

As indicated above, thermally conductive element 16 is preferably made relatively massive (as compared to handle 14) so that it will be able to achieve a high thermal potential. In other words, a more massive element 16 will be able to draw more heat from the user's skin for a longer period of time. This means that the user can effectively numb a greater amount of skin before having to re-chill applicator 12.

Once chilled, applicator 12 may be used alone, as shown in FIG. 3, which is preferred, to cool the user's skin surface, or alternatively, the applicator may be shaped and adapted to be secured to a skin/hair-treatment device 28 (see FIGS. 4 and 5), such as the above-described depilator, hair shaver, or skin exfoliator, or some other device. As applicator 12 is used, its cold contact surface 17 will draw heat from the user's skin, creating a desired numbing effect immediately adjacent to the regions of the skin that are, or soon will be treated by the skin/hair treatment device 28. As mentioned above, the numbed areas reduce pain caused by the skin/hair treatment device 28. Eventually, the contact surface 17 and the entire thermally conductive element 16 will warm and will loose its effectiveness at numbing the user's skin. At this point, the user reinserts the thermally conductive element 16 of applicator 12 into the expansion chamber 20 of base unit 10 so that applicator 12 may be re-chilled and less-painful skin treatment may continue. Thus, if the applicator 12 is attached to another device (such as a depllilator, as shown in FIG. 5), it can be detached (see FIGS. 3 and 4) or just manipulated (e.g., rotated) to permit the conductive element to be chilled in the base 10.

The above-described applicator 12 is selectively chilled by the base unit 10 through the controlled, yet rapid expansion of a fluid under pressure. A pressurized gas, preferably $CO_2$ or nitrogen, which may be stored in a gaseous or liquid form is delivered from tank 26 in a desired amount to an environment of greatly reduced pressure, such as the atmosphere (e.g., a change of around 20 pounds per square inch to atmospheric pressure). As understood by those skilled in the art, the expansion of the gas is accompanied by an endothermic reaction, which causes heat to be removed from whatever comes in contact with the just-expanded gas.

As shown in FIGS. 2 and 6, tank 26 is connected to valve assembly 22, which in turn, is connected to expansion assembly 19 so that when valve 22 is opened using trigger 24, pressurized gas from tank 26 is forced through valve assembly 22 and into expansion assembly 19. More specifically, as shown in FIG. 6, expansion assembly 19 includes an inlet port 30 and several outlet ports 32. Also shown in FIG. 6, coupling 25 of the valve assembly 22 includes an inlet connection 34 and an outlet connection 36. Tank 26 includes an outlet fitting 38 which is releasably connected to inlet connection 34 of coupling 25 and, as also shown, outlet connection 36 of coupling 25 is connected to inlet port 30 of expansion assembly 19. With this arrangement, the pressurized gas located in tank 26 will remain there until trigger 24 is depressed (or the valve assembly 22 is otherwise opened). At that point, the pressurized gas will quickly flow from tank, through coupling 25 and into inlet port 30 of expansion assembly 19. As shown in FIG. 6, both inlet port 30 and outlet ports 32 of expansion assembly 19 are in fluid communication with the expansion chamber 20 so that as the gas expands into the expansion chamber, the expanding gas will draw heat from whatever is located within the expansion chamber 20.

The pressurized tank 26 serves as a replenishable source of gas under pressure. The tank 26, to be used can be constructed so as to be refillable by the user, but in the described embodiment it is simply replaced when the gas supply is exhausted. This is presently preferred because users do not require any special instructions to replenish the gas source. The pressurized tank 26 includes a valve 34, e.g., a check valve, through which fluid is released in either gaseous or liquid form to achieve the rapid chilling effect described herein. The same valve can permit refilling of the tank in certain embodiments, if desired. Although it is preferred that tank 26 include a one-way check valve 34, alternative to the check valve 34, tank may include a one-time rupturable metal cap. In such instance, inlet connection 34 of coupling 25 would include a puncturing element (not shown in any detail shaped and arranged so that as tank 26 is threaded into locking engagement with corresponding threads of inlet connection 34, rupturing metal cap would be forced to overlap with puncturing element (not shown) so that puncturing element would rupture metal cap and allow the gas located within tank 26 to advance through valve assembly 22, as demanded (i.e., when valve assembly 22 is opened). This arrangement is well known and used often in devices and systems where a tank of pressurized gas is used in connection with a device, such as an air-powered pistol. If a check valve is used in the tank, the puncturing element would be replaced with a pressing element (also not shown). The pressing element would activate the check valve of the tank 26, but only when the tank 26 is sufficiently secured to the inlet connection 34 and sealed by conventional o-rings, for example, as is also well known by those skilled in the art.

Tank 26 is designed to snugly fit into tank-cavity 18 of base unit 10. Tank-cavity 18 may be either horizontally disposed or angled slightly downward so that tank 26, when inserted into tank-cavity 18 will reside either horizontal or angled slightly downward. In this latter arrangement, any liquefied portion of the compressed gas will be expelled through the valve 22, when valve 22 is opened. This will result in a very quick chilling of the thermally-conduct element 16; however, it may result in a quicker depletion of the fluid within the tank 26. Because of this, a horizontal orientation of tank 26 (or even an upright angle) is preferred so that only gas is expelled from tank 26 when valve 22 is opened.

As mentioned above, the expansion chamber 20 is sized and shaped to receive the thermally conductive element 16 of applicator 12. It is preferred that expansion chamber 20 is sized larger than thermally conductive element 16 so that as gas from tank 26 quickly flows into and expands within expansion chamber 20, thermally conductive element 16 will not substantially alter the rate of gas flow from inlet port 30 to outlet ports 32, nor prevent or restrict the expansion of the gas so that maximum heat-absorption is achieved. The gas entering expansion chamber 20 is encouraged to flow from inlet port 30 to outlet ports 32 passing by the inserted thermally conductive element 16. The chilled and expanding gas is discouraged from discharging from expansion chamber 20 through the upper insertion opening 40. This can be accomplished by designing the shape and size of the rim of the insertion opening 40 to be a close tolerance fit with respect to the size and shape of the thermally conductive element 16. An appropriate rubber element may be further provided along the rim of the insertion opening 40 so that a relatively tight seal is created when the thermally conductive element 16 is inserted into the insertion opening 40, discouraging the escape of gas entering into the expansion chamber 20 through the insertion opening 40.

Once gas from tank 26 leaves expansion chamber 20 through outlet ports 32, gas is preferably directed to the relatively large and empty space located within housing of base unit 10. This space allows the released gas to freely expand and equilibrate with the surrounding environment without causing any damage the user. The housing of the base unit 10 preferably includes an appropriate vent (not shown) to allow accumulated gas within the housing to escape.

Tank 26 is preferably made from metal and must be designed to safely contain the desired amount of gas at the desired pressure, as understood and regularly practiced by those skilled in the art. Such pressurized tanks of a variety of shapes and sizes are commercially available today. The present invention may be easily adapted to accommodate any such pressurized tank. Of course, the more volume of gas located within tank 26, the more thermal energy the contained gas will effectively absorb when released into the atmosphere. Also, the smaller tank 26 is, the higher the pressure any given volume of gas will be. The higher the pressure of the gas contained within tank 26, the stronger the tank must be. The present invention does not demand any particular size or shape of tank 26 to perform as described. However, this being said, convenience will force tank 26 to be small and its contained gas pressure high, while cost and safety will yield a larger tank size with lower pressures, yet a greater volume of gas. Applicants recommend a balance of the parameters when selecting a suitable tank size.

Valve 22 has been shown in the figures as an illustrative device (i.e., not shown in detail—without conventional O-ring seals, threading, and the like). Suitable valves are readily available and understood and any of many different types of valves can be implemented to the present invention. The purpose of whatever valve is selected is simple—the valve 22 must connect to the outlet fitting 38 of tank 26 and seal and contain the pressurized gas so as to prevent flow through the outlet connection 36 until the valve 22 is selectively opened. The valve as shown in the drawings and described in the present specification is a trigger 24, which is mechanically connected to the valve mechanism so that upon displacing the trigger 24, valve 22 will open and will thereby cause the release of pressurized gas from tank 26, through valve 22 and into inlet port 30 of expansion assembly 19, as described above.

Other features of valve 22 contemplated by applicants include electronic control of the valve 22 and automatic controlled release of a prescribed amount of gas so that when trigger 24 is actuated, for example, the valve will open for a time period of only 1 second before automatically closing. The user then depresses the trigger 24 as many times as desired to chill the applicator to his or her preference; however, a limiter can be provided to regulate valve movement and thereby prevent the user from over-chilling and wasting gas. For example, a secondary valve which changes to a closed state when cooled below a prescribed temperature can be provided, such as a memory-metal alloy (e.g., nitinol) valve having a material composition, processing history, and training suitable to provide desired operation at the prescribed temperature.

Optionally, valve 22 can move between a no-flow rate (closed) and a maximum-flow rate (wide open), either by operation of a manual control such as a knob or lever, or by operation of control circuitry 23 (see FIG. 1) coupled to a motor, solenoid, or other electrically or mechanically controllable element.

Also, applicants contemplate having a valve 22 automatically activated in response to the user fully inserting the thermally conductive element 16 into expansion chamber 20 (i.e., in response to pressure). In such an arrangement, a trigger 24a is positioned so as to be engaged upon insertion of the conductive element 16 into the base 10, as shown in FIG. 1 as an alternative to having trigger 24. In this arrangement, therefore, the trigger need not be exteriorly disposed on the housing of the base, or be actuated by the user. Instead, it can be actuated by features associated with the applicator 12, such as the conductive element 16.

As a safety feature, referring to FIG. 6, the shape of expansion chamber 20 (at least the insertion opening 40 through which thermally conductive element fits) is keyed so that only the shape of the thermally conductive element 16 can fit. To further prevent or discourage insertion of anything other than thermally conductive elements 16 into insertion opening 40, a center post 42 is preferably provided in the expansion chamber 20, arranged as a protrusion to purposely block a portion of the entryway into the chamber 20. The size and shape of the protrusion is such that it will automatically align with and be received into bore 16b of thermally conductive element 16, (see FIG. 3). As illustrated, the center post 42 and bore 16b function as a "key" system to discourage any item other than the thermally conductive element from being inserted into expansion chamber 20. Of course, the key-structure of this feature may vary considerably in that post 42 does not have to be centrally located within the chamber 20 and similarly bore 16b does not have to be located in the center of the thermally conductive element 16. Such components can be positioned in any orientation and can be any appropriate size and shape, as long as together these mating components create a keying effect which allows only the thermally conductive element to enter the expansion chamber and further prevents entry of a child's fingers, for example.

It is preferred that the path of fluid flow from supply tank 26 through valve 22 and into expansion chamber 20 include no sharp angles or bends since such sharp traverses can cause the flowing gas to sublimate directly to form dry ice, in the case of $CO_2$, which could quickly (although temporarily) clog the system and prevent any further flow of gas from reaching the expansion chamber or just reduce performance of the applicator/base system. Gas from tank 26 is directed through the expansion chamber 20 to the outlet ports In use, the thermally conductive element of the applicator is positioned in the path of the just expelled gas, and so the controlled release of gas results in a rapid chilling of the element. Once this element is chilled as desired or to a predetermined temperature, the applicator is handled so that the conductive element 16 contacts or remains in contact with the user's skin and provides a cooling effect without the need for ice. The chilled element draws heat from the user's skin through conduction and the resulting decrease in temperature of the user's skin helps desensitize the skin. Thus, for example, any pain resulting from the extraction of the user's hair can be mitigated.

Referring now to FIG. 7, a skin-treating device 50 according to another embodiment of the invention is shown. According to this embodiment, a supply of compressed gas is located within the hand-held device 50 so that a chilling effect can be created on the hand-held device itself, instead of requiring the use of a base unit. One benefit to such an assembly is that the chilling effect can be sustained or maintained for a longer period of time without interruption to the user.

Device 50 is shown in FIG. 7 with a housing 52 that is open so that its interior can be viewed for the purpose of explaining its structure and operation. According to this embodiment of the invention, device 50 includes an onboard supply of compressed gas (such as $CO_2$) stored in a tank 54, a connector 56, a conduit 58, an expansion chamber 60, a contact surface 62, and a control valve 64. Tank 54 is connected to connector 56 either permanently or in a removable manner. If tank 54 is intended to be removable, for example, if tank 54 is a one-time use structure, then tank 54 can include a rupturable cap and a neck that might include threads and connector 56 would include a bore having a cap-rupturing pin and mating structure such as threads. With this disposable arrangement, a user engages the connector 56 and the neck of tank 54 by rotation, if it is a threaded connection, or by axial movement, if it is a compression fitting, until the pin ruptures the cap of the tank and thereby releases the stored gas into the fluid system of the device 50, as described below.

Tank 54 can also be permanently connected to connector 56. In such instance, tank 54 is refilled with compressed gas using a larger external supply of greater pressure. The connectors, valves and seals which would be required to allow tank 54 to be refilled using an external source are neither disclosed nor described in any great detail because such structure and operation is readily understood by those of skill in the art. Such systems are used in many devices including refillable butane-powered cigarette lighters. The important feature here is that the onboard tank 54 of this embodiment can have an arbitrary shape if designed to be refilled using an external and separate supply of pressurized gas.

According to this embodiment, tank 54 is smaller in size than tank 16 discussed above and shown in FIGS. 1-6. Applicants contemplate using a tank size that can hold between 20 and 30 grams of $CO_2$ gas for this onboard-tank embodiment.

Regardless of the particulars of tank 54, its pressurized gas is in fluid connection with expansion chamber 60 through conduit 58 and valve 64.

In use of device 50, a user pre-chills contact surface 62 prior to contacting the device to his or her skin. To chill the contact surface 62, the user opens valve 64, preferably in a pulsed manner so that a predetermined quantity of pressurized gas passes from pressurized tank 54 through connector 56, into conduit 58, through valve 64 and into expansion chamber 60. Expansion chamber 60 is preferably formed integrally with contact surface 64 and is made from a dense, thermally conductive material, such as steel or copper or bronze. Expansion chamber 60 is preferably a relatively large open chamber so that the pressurized gas entering from valve 64 and conduit 58 can quickly expand and thereby absorb heat from the side walls and the contact surface 62 of the expansion chamber 60. An appropriate venting port 66 may be used to release the gas accumulating within the chamber 60 to prevent the pressure within the chamber from getting too high so as to restrict the expansion efficiency of the entering gas. A personal care appliance can be supported on the device 50, such as a motor 68 driving a cutter 70 of a depilator device of the type described above Applicants further contemplate using appropriate electronic controlling circuitry 23 to control the flow of pressurized gas from the tank 54 (or tank 26 of the previous embodiment) to maximize thermal transfer efficiency so that the gas within the tank is not wasted. Circuitry 23 could include a timing circuit that would pulse the gas from the tank to its expansion chamber at a predetermined rate and duration depending on the desired temperature of the contact surface, as set by the user, and the ambient temperature, as measured by the circuit and an appropriate sensor. The circuit 23 could limit the flow of the gas using electro-magnet controlled valves, all of which are well known by those skilled in the art.

In the above-described preferred embodiment (shown in FIGS. 1-6), the flow of gas from the tank 26 to the expansion chamber 20 can be automatic so that the user merely has to insert the thermally conductive element into the expansion chamber 20 to activate the chilling process (i.e., turn on the flow of gas from tank 26). The system would then chill the inserted element automatically for a predetermined length of time after which an appropriate indicator light or sound (including simply the sound that the flow of gas has stopped) would indicate that a consistent usable temperature of the contact surface has been reached and that the device can be again applied to the user's skin. Alternatively, the flow of gas from the tank to the expansion chamber can be opened and closed by the insertion and removal of the thermally conductive element into and out from the expansion chamber, respectively.

As is well understood by those of skill in the art, the systems described in this application handle pressurized gas and all of the components of the device will or can experience severe temperature variations, from room temperature down to around about −70° F. and then back to room temperature. To this end, appropriate reinforcement and insulation must be applied in a manner known to those of the art so that such a temperature gradient, and high pressures and the formation of ice due to collected condensation on chilled components within the system and dry ice owing to quickly expanded $CO_2$ gas within the system is safely controlled and damage to the components of the system prevented.

Applicants further contemplate that thermally conductive element 16 can be moveably supported on the applicator 12 or device 50. Thus, conductive element 16 can be structured as a rotating element so that it may be rolled along the surface of the user's skin and so that only a small changing portion of the rolling element touches the user's skin at any given time. Also, an appropriate liquid may be supplied within a sealed chamber 15 located within the thermally conductive element (see FIG. 3). Such a liquid can be chilled by the base unit and further used to store the heat-absorbing potential for a longer period of time than if just a metal were used as the thermally conductive element. Such an appropriate liquid would be similar to the liquid used in the commercially available sports-injury cold-packs, and is well known by those skilled in the art. Further, the conductive element 16 or the surface 16a thereof can be flexible to facilitate tracking skin contours as the device 50 or applicator 12 is moved across a skin surface.

While the invention has been illustrated in detail with particular reference to certain embodiments thereof, and described in connection with the illustrated embodiments and variations thereof, the invention is capable of different embodiments and insubstantial variations, and its details are capable of modifications in various obvious respects, including using parts of one embodiment in connection with another embodiment. As will be readily apparent to those skilled in the art, variations and modifications can be affected while remaining within the spirit and scope of the invention. Accordingly, the accompanying drawing figures and the foregoing written description of certain embodiments and their variations are for illustrative purposes only, and do not in any way limit the invention, which is defined only by the claims.

We claim:

1. A skin treatment system, comprising:
   (a) a handle;
   (b) an applicator supported by the handle, the applicator including a thermally conductive element;
   (c) a base unit comprising at least a housing;
   (d) a gas expansion chamber supported by the base unit and having an insertion opening sized to receive at least the thermally conductive element of the applicator;
   (e) a coupling supported by the base unit and connectable to a supply of pressurized fluid for providing the pressurized fluid into the expansion chamber; and
   (f) a valve, disposed in the fluid path between the supply and the expansion chamber so as to control release of any pressurized fluid into the expansion chamber,
   so that the thermally conductive element of the applicator is cooled by the release of pressurized fluid into the expansion chamber.

2. The skin treatment system of claim 1, wherein the thermally conductive element of the applicator is both separable from the base unit and insertable into the opening of the gas expansion chamber that is supported by the base unit.

3. The skin treatment system of claim 1, wherein the insertion opening is keyed to the shape of at least a portion of the applicator.

4. The skin treatment system of claim 1, wherein the thermally conductive element of the applicator has an outer layer made of a material different than the thermally conductive element.

5. The skin treatment system of claim 4, wherein the outer layer comprises a smooth surface made of one of nylon, polyvinyl, Teflon, or other plastic.

6. The skin treatment system of claim 1, wherein the applicator is movably supported on the handle.

7. The skin treatment system of claim 1, wherein at least a portion of the thermally conductive element of the applicator comprises a flexible skin-contacting surface suitable for tracking skin contours as the appliance is moved across a skin surface.

8. The skin treatment system of claim 1, wherein the applicator further comprises a sealed chamber containing a fluid in conductive communication with the expansion chamber so as to store a heat-absorbing potential.

9. The skin treatment system of claim 1, wherein the handle supports a housing that comprises a means for performing a personal care operation.

10. The skin treatment system of claim 9, wherein the performing means is disposed proximate to the applicator.

11. The skin treatment system of claim 9, wherein the housing is detachably supported on the handle.

12. The skin treatment system of claim 1, wherein the expansion chamber further comprises at least one fluid discharge port.

13. The skin treatment system of claim 1, wherein the handle is made of a thermally insulative material.

14. The skin treatment system of claim 1, further comprising a trigger operative to open the valve.

15. The skin treatment system of claim 14, wherein the valve opens under circuitry control in response to operation of the trigger.

16. The skin treatment system of claim 14, wherein the valve opens automatically in response to a user fully inserting the thermally conductive element into the expansion chamber into contact with the trigger.

* * * * *